(12) United States Patent
Young (10) Patent No.: US 9,888,728 B1
(45) Date of Patent: Feb. 13, 2018

(54) UNDERGARMENT WITH CATHETER SUPPORT

(71) Applicant: Yvette S. Young, Detroit Lakes, MN (US)

(72) Inventor: Yvette S. Young, Detroit Lakes, MN (US)

( * ) Notice: Subject to any disclaimer, the term of this patent is extended or adjusted under 35 U.S.C. 154(b) by 159 days.

(21) Appl. No.: 14/257,184

(22) Filed: Apr. 21, 2014

Related U.S. Application Data

(60) Provisional application No. 61/814,432, filed on Apr. 22, 2013.

(51) Int. Cl.
*A41B 9/00* (2006.01)
*A61M 25/00* (2006.01)

(52) U.S. Cl.
CPC .............. *A41B 9/00* (2013.01); *A61M 25/00* (2013.01)

(58) Field of Classification Search
CPC ...... A61F 5/453; A61F 5/455; A61F 13/4915; A61F 13/491; A41B 9/00; A61M 25/00
See application file for complete search history.

(56) References Cited

U.S. PATENT DOCUMENTS

| | | | |
|---|---|---|---|
| 4,221,215 A * | 9/1980 | Mandelbaum | A61F 13/02 128/DIG. 26 |
| 4,378,010 A | 3/1983 | McDonald | |
| 4,460,356 A * | 7/1984 | Moseley | A61M 25/02 604/180 |
| 4,471,772 A | 9/1984 | Miller, Jr. | |
| 4,526,167 A | 7/1985 | Ebenal | |
| 4,553,968 A | 11/1985 | Komis | |
| 4,666,432 A | 5/1987 | McNeish | |
| 4,732,146 A * | 3/1988 | Fasline | A61F 13/0269 602/79 |
| 5,366,449 A | 11/1994 | Gilberg | |
| 5,843,065 A | 12/1998 | Wyant | |
| 6,014,777 A | 1/2000 | Gupton | |
| 8,607,366 B2 | 12/2013 | Austin | |
| 8,696,642 B1 * | 4/2014 | Price | A61F 13/4915 604/385.09 |
| 9,119,749 B2 * | 9/2015 | Close | A61F 13/49007 |
| 2010/0137805 A1 | 6/2010 | Farchione | |
| 2013/0006208 A1 * | 1/2013 | Close | A61F 13/471 604/385.09 |

* cited by examiner

*Primary Examiner* — Anna Kinsaul
(74) *Attorney, Agent, or Firm* — Neustel Law Offices (57) ABSTRACT

An undergarment with catheter support which increases comfort and reduces the risk of complications related to placement of indwelling catheter tubing. The undergarment with catheter support generally includes a rear portion, a first panel extending from the rear portion and a second panel extending from the rear portion. The rear portion is adapted to be positioned underneath the buttocks of a patient, with the first and second panels being extended around the legs of the patient before connecting to the rear portion so as to form a unified undergarment configuration. The first and second panels are connected to each other via slot connectors to define a catheter slot through which a catheter tube may be extended. A tube retainer and/or tube adapter may also be utilized to guide the catheter tube out of the undergarment through the catheter slot.

13 Claims, 10 Drawing Sheets

UNDERGARMENT WITH CATHETER SUPPORT

CROSS REFERENCE TO RELATED APPLICATIONS

I hereby claim benefit under Title 35, United States Code, Section 119(e) of U.S. provisional patent application Ser. No. 61/814,432 filed Apr. 22, 2013. The 61/814,432 application is hereby incorporated by reference into this application.

STATEMENT REGARDING FEDERALLY SPONSORED RESEARCH OR DEVELOPMENT

Not applicable to this application.

BACKGROUND OF THE INVENTION

Field of the Invention

The present invention relates generally to a catheter support and more specifically it relates to an undergarment with catheter support which increases comfort and reduces the risk of complications related to placement of indwelling catheter tubing.

Description of the Related Art

Any discussion of the related art throughout the specification should in no way be considered as an admission that such related art is widely known or forms part of common general knowledge in the field.

Catheter tubing is commonly used in medical settings such as in hospitals and hospices. Often such tubing enters or exits the body of the patient in or around the groin. Traditionally, the catheter tubing is merely threaded through leg openings, such as the leg opening of a diaper. Such positioning can lead to increased discomfort for the patient by increasing the risk for leakage, skin breakdown, and occlusion. Additionally, the pressure caused by the catheter tubing being pressed down as it exits the legging can increase pain and risk of displacement.

Because of the inherent problems with the related art, there is a need for a new and improved undergarment with catheter support which increases comfort and reduces the risk of complications related to placement of indwelling catheter tubing.

BRIEF SUMMARY OF THE INVENTION

The invention generally relates to an undergarment which includes a rear portion, a first panel extending from the rear portion and a second panel extending from the rear portion. The rear portion is adapted to be positioned underneath the buttocks of a patient, with the first and second panels being extended around the legs of the patient before connecting to the rear portion so as to form a unified undergarment configuration. The first and second panels are connected to each other via slot connectors to define a catheter slot through which a catheter tube may be extended. A tube retainer and/or tube adapter may also be utilized to guide the catheter tube out of the undergarment through the catheter slot.

There has thus been outlined, rather broadly, some of the features of the invention in order that the detailed description thereof may be better understood, and in order that the present contribution to the art may be better appreciated. There are additional features of the invention that will be described hereinafter and that will form the subject matter of the claims appended hereto. In this respect, before explaining at least one embodiment of the invention in detail, it is to be understood that the invention is not limited in its application to the details of construction or to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

A. Overview.

Turning now descriptively to the drawings, in which similar reference characters denote similar elements throughout the several views, FIGS. 1 through 10 illustrate an undergarment with catheter support 10, which comprises a rear portion 20, a first panel 30 extending from the rear portion 30 and a second panel 40 extending from the rear portion 40. The rear portion 20 is adapted to be positioned underneath the buttocks of a patient, with the first and second panels 30, 40 being extended around the legs of the patient before connecting to the rear portion 20 so as to form a unified undergarment 10 configuration. The first and second panels 30, 40 are connected to each other via slot connectors 55, 56, 57 to define a catheter slot 50 through which a catheter tube 15 may be extended. A tube retainer 60 and/or tube adapter 70 may also be utilized to guide the catheter tube 15 out of the undergarment 10 through the catheter slot 50.

B. Undergarment.

As shown throughout the figures, the present invention comprises an undergarment 10 which includes a rear portion 20, a first panel 30 extending from the rear portion 20, and a second panel 40 extending from the rear portion 20. The rear portion 20 and both panels 30, 40 are preferably comprised of an integral structure, with the entire body of the undergarment 10 comprising a flexible material. The undergarment 10 is preferably at least partially comprised of a material and configuration which will act as an absorbent for body fluids and the like, such as those resulting from urination or defecation.

Figure 2:
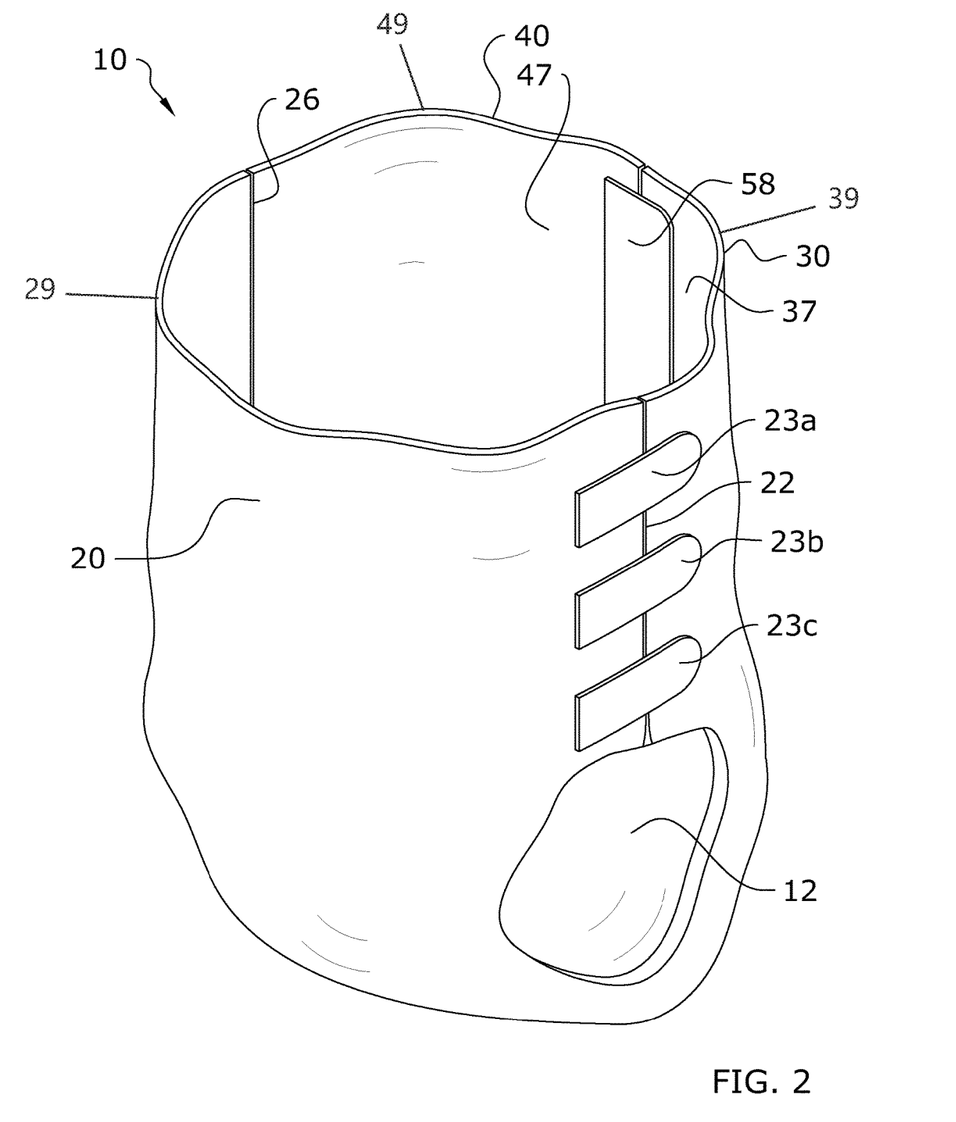
FIG. 2 is a rear upper perspective view of the present invention.

As shown in the figures, the rear portion 20 is adapted to extend around the buttocks of an individual. The rear portion 20 of the undergarment 10 comprises a semi-circle cross-section as shown in FIG. 2 which combines with the first and second panels 30, 40 to form the unitary undergarment 10. At least a portion of the rear portion 20 will be comprised of an absorbent material so as to act as a diaper for any incontinence.

Figure 8:
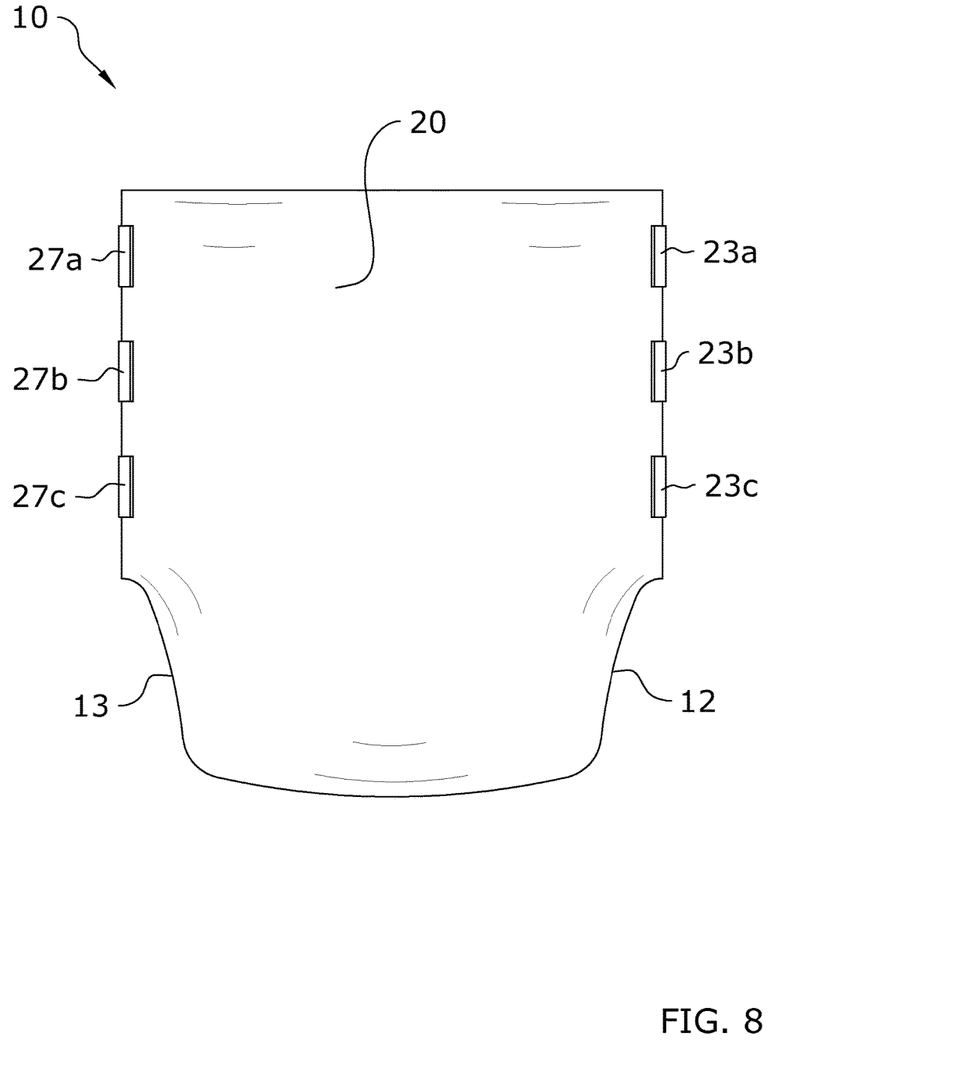
FIG. 8 is a rear view of the present invention.
Figure 9:
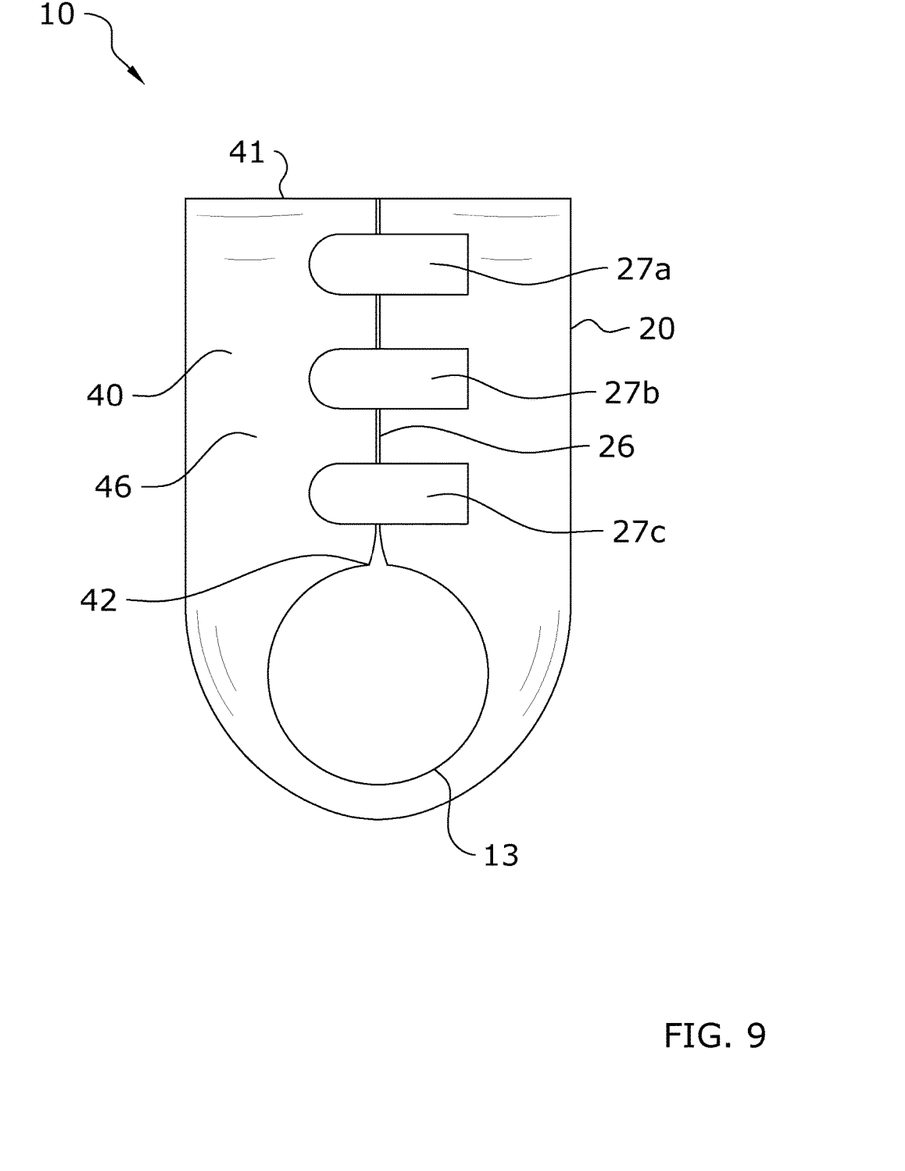
FIG. 9 is a first side view of the present invention.
Figure 10:
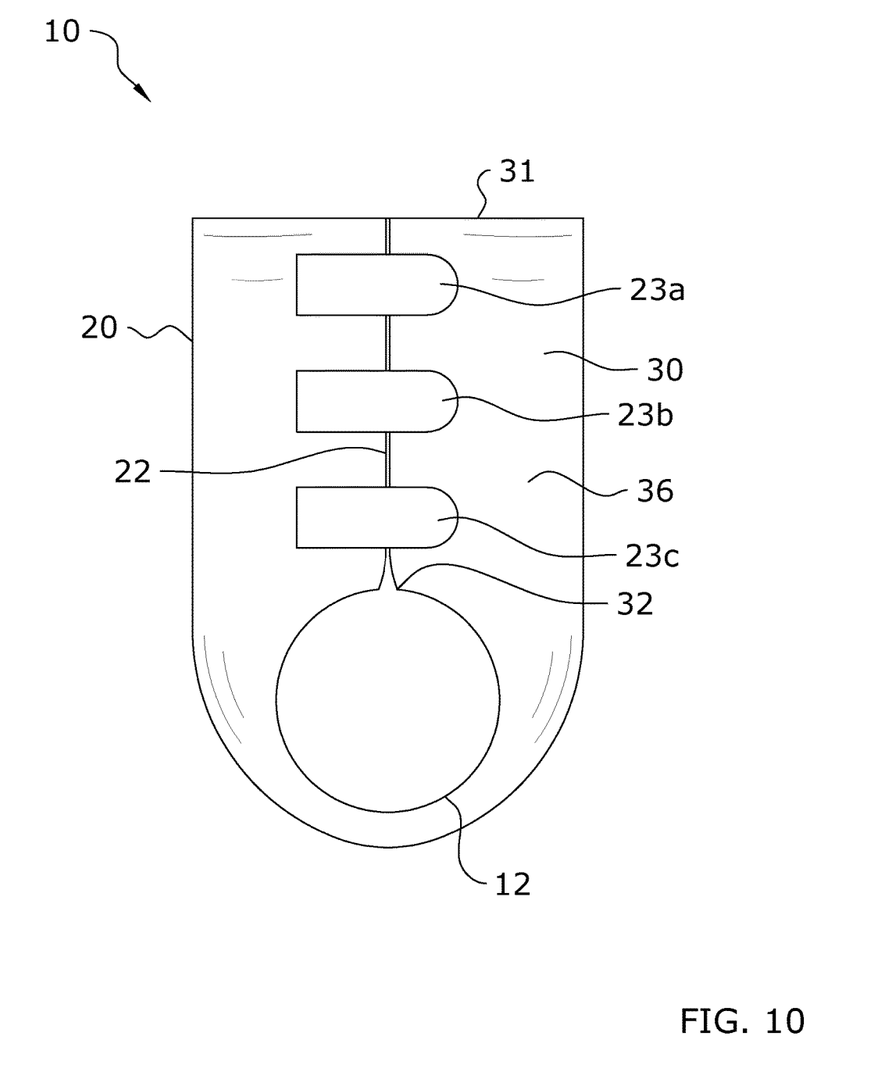
FIG. 10 is a second side view of the present invention.

The rear portion 20 includes a first side 22 and a second side 23. The first side 22 of the rear portion 20 is connected to the first panel 30 when the undergarment 10 is worn as shown in FIG. 8. Similarly, the second side 23 of the rear portion 20 is connected to the second panel 40 when the undergarment is worn as shown in FIG. 9. The use of panels 30, 40 adapted to removably connect to the rear portion 20 aids in applying or removing the undergarment on immobile patients, such as those who are bedridden.

In the figures, first connectors 23a, 23b, 23c are utilized to connect the first panel 30 with the first side 22 of the rear portion 20. Similarly, second connectors 27a, 27b, 27c are utilized to connect the second panel 40 with the second side 23 of the rear portion 20. Various methods, devices and the like may be utilized to connect the rear portion 20 with the first panel 30 and the second panel 40. By way of example, clasps, buttons, bands, adhesives, straps, and the like may all be utilized in different embodiments to removably secure the first and second panels 30, 40 to the rear portion 20 and thus complete the undergarment 10.

The first panel 30 is best shown in FIG. 2. As shown therein, the first panel 30 extends from a first side of the rear portion 22. In a preferred embodiment as shown, the first panel 30 will be integrally formed with the rear portion 22 of a unitary structure. The first panel 30 includes an upper end 31, lower end 32, first side 33, and a second side 34. The first panel 30 also includes an outer surface 36 and an inner surface 37, the inner surface 37 being at least partially comprised of an absorptive material.

The upper end 31 of the first panel 30 partially forms the waistband of the undergarment 10. The lower end 32 includes a curved portion on the second side 34 of the first panel 30 to accommodate a first leg opening 12 when the undergarment 10 is formed. The first side 33 of the first panel 30 is removably connected to the first side 22 of the rear portion 20 by one or more first connectors 23a, 23b, 23c. The second side 34 of the first panel 30 is removably connected to the first side 43 of the second panel 40 by one or more slot connectors 55, 56, 57 as discussed below.

As best shown in FIG. 2, the second panel 40 extends from a second side of the rear portion 22. In a preferred embodiment as shown, the second panel 40 will be integrally formed of a unitary structure with the rear portion 22 and the first panel 30. The second panel 40 includes an upper end 41, a lower end 42, a first side 43, and a second side 44. The second panel 40 also includes an outer surface 46 and an inner surface 47, the inner surface 47 being at least partially comprised of an absorptive material.

The upper end 41 of the second panel 40 partially forms the waistband of the undergarment 10. The lower end 42 includes a curved portion on the second side 44 of the second panel 40 to accommodate a second leg opening 13 when the undergarment 10 is formed. The first side 43 of the second panel 40 is removably connected to the second side 34 of the first panel 30 by one or more slot connectors 55, 56, 57 as discussed below. The second side 44 of the second panel 40 is removably connected to the second side 26 of the rear portion 20 by one or more second connectors 27a, 27b, 27c. As shown in FIG. 2, the first and second panel upper edges (39, 49) are adapted to releasably connect to the rear portion upper edge (29) forming the undergarment's upper edge which is adapted to encircle the waist.

As shown throughout the figures, a catheter slot 50 is defined between the first panel 30 and the second panel 40 when the panels 30, 40 are interconnected together. The catheter slot 50 preferably extends vertically between the upper and lower ends 31, 32, 41, 42 of the front of the undergarment 10 when fully formed such as shown in FIGS. 1 and 3-6. The catheter slot 50 is generally formed when the first panel 30 is connected to the second panel 40 via one or more slot connectors 55, 56, 57.

The catheter slot 50 is adapted to allow a catheter tube 15 or other medical instrument or device to pass through the catheter slot 50 as shown in the figures. The present invention is preferably utilized with an indwelling catheter which comprises a catheter tube 15 having an end inserted subcutaneously. The distal end of the catheter tube 15 extends through the catheter slot 50 and, in some embodiments, a tube retainer 60 or adapter 70.

Figure 1:
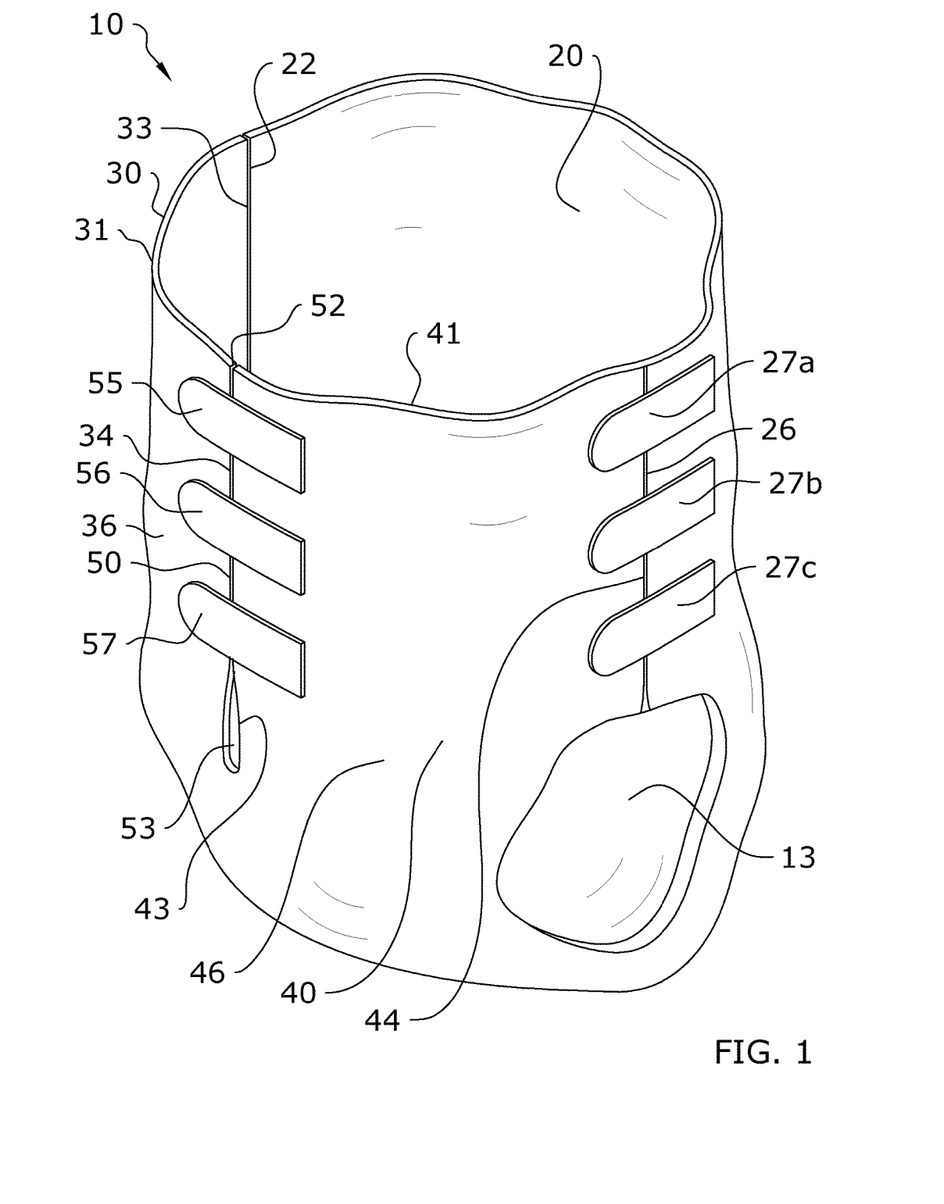
FIG. 1 is a frontal upper perspective view of the present invention.

As best shown in FIG. 1, the catheter slot 50 includes an upper end 52 and a lower end 53. The upper end 52 of the catheter slot 50 is flush with the upper ends 31, 41 of the first and second panels 30, 40. The lower end 53 of the catheter slot 50 is adjacent the lower ends 32, 42 of the first and second panels 30, 40. The catheter tube 15 may extend through any portion of the catheter slot 50 between its upper and lower ends 52, 53.

As best shown in FIG. 2, the present invention may include a pad 58 which is adapted to be positioned behind the catheter slot 50 between the body of the patient and the undergarment 10. The pad 58 is generally comprised of a piece of fabric or other material which is adapted to be positioned behind the portions of the catheter slot 50 that the catheter tube 15 is not passing through. The pad 58 acts to prevent exposure of the skin of the patient if the catheter slot 50 puckers or otherwise opens up during usage, such as when moving the patient.

As shown throughout the figures, one or more slot connectors 55, 56, 57 link the first and second panels 30, 40 to define the catheter slot 50 therebetween. The slot connectors 55, 56, 57 may be comprised of various configurations. By way of example, clasps, buttons, bands, adhesives, straps, and the like may be utilized for the slot connectors 55, 56, 57.

In a preferred embodiment, a first slot connector 55 extends across the upper end 52 of the catheter slot 50, a second slot connector 56 extends across a central portion of the catheter slot 50, and a third slot connector 57 extends across the lower end 53 of the catheter slot 50. This configuration allows for multiple positions for the catheter tube 15 to be placed when exiting the undergarment 10. The number of slot connectors 55, 56, 57 may vary in different embodiments, with two slots connectors 55, 56 being preferable in some applications of the present invention.

Figure 3:
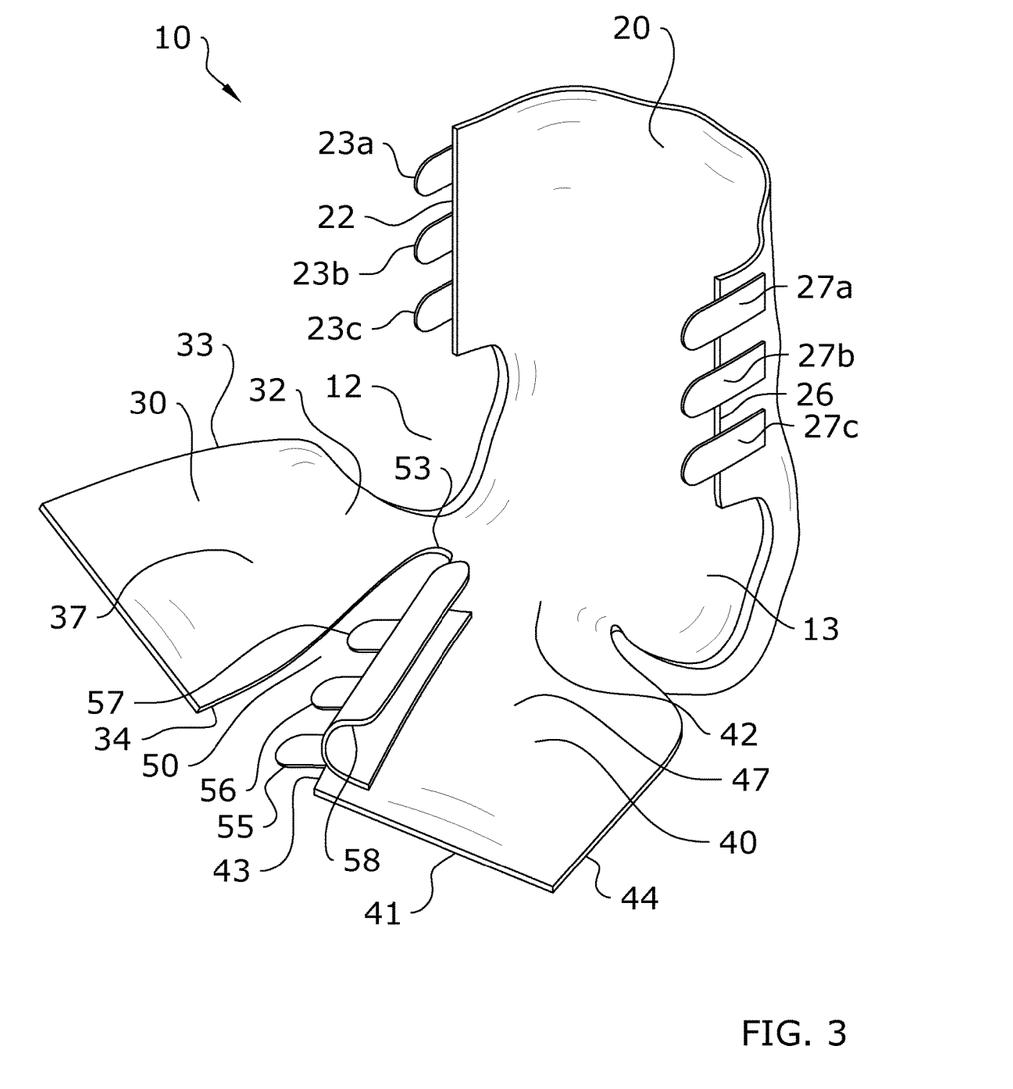
FIG. 3 is an upper perspective view of the present invention with the panels pulled away from the rear portion.
Figure 4:
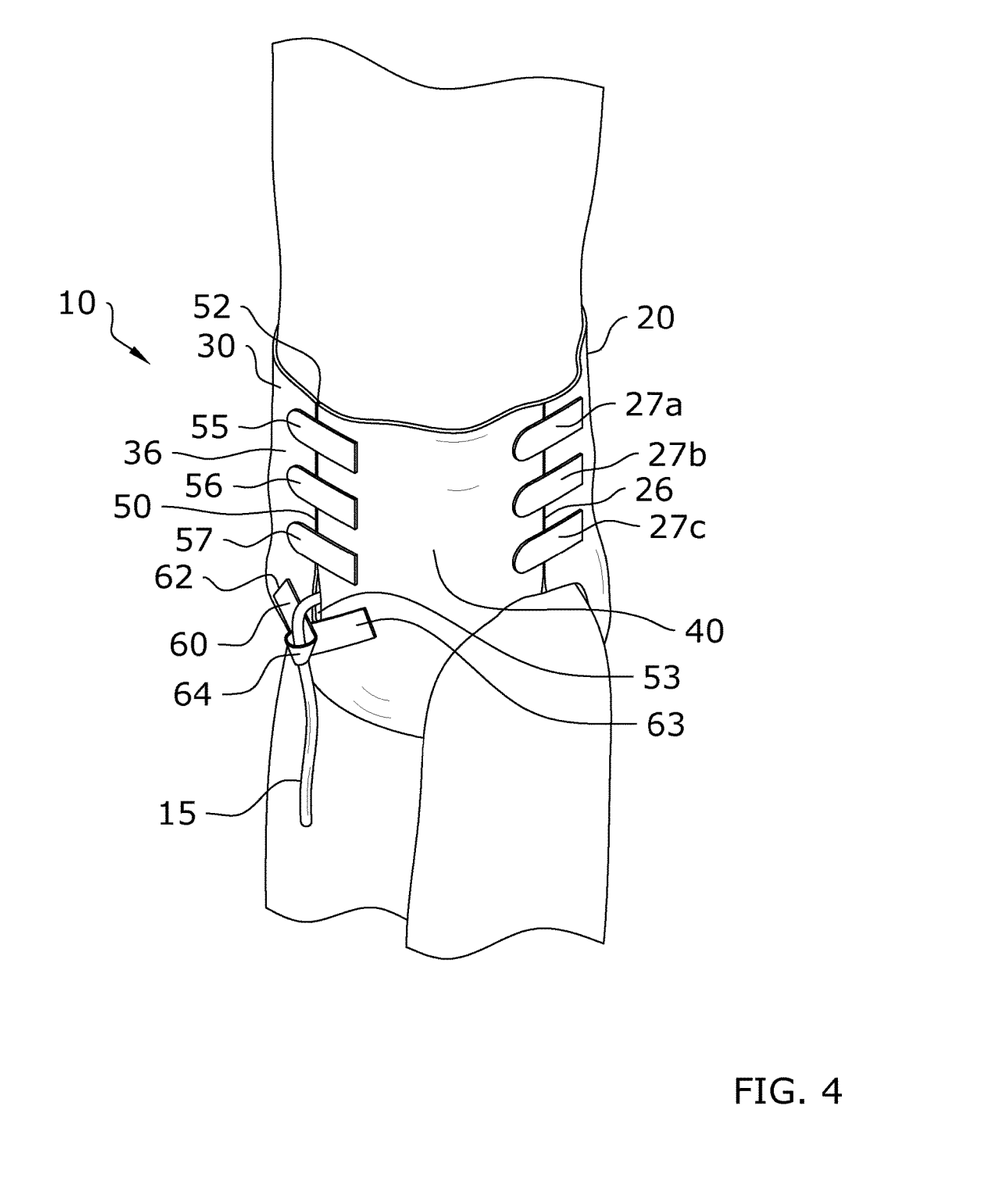
FIG. 4 is an upper perspective view of the present invention being worn and in use.

As shown in FIG. 3, a tube retainer 60 may be utilized to guide the catheter tube 15 as it exits the catheter slot 50. The tube retainer 60 may be comprised of an elongated, tab-shaped member having a first end 62 and a second end 63. The first end 62 of the tube retainer 60 is removably connected to the first panel 30 and the second end 63 is removably connected to the second panel 40.

The respective ends 62, 63 of the tube retainer 60 may include an adhesive or hook-and-loop fastener configuration to allow the tube retainer 60 to be removably secured across the catheter slot 50. The tube retainer 60 includes a looped portion at its central area which forms a central opening 74 through which the catheter tube 15 may be positioned.

Figure 5:
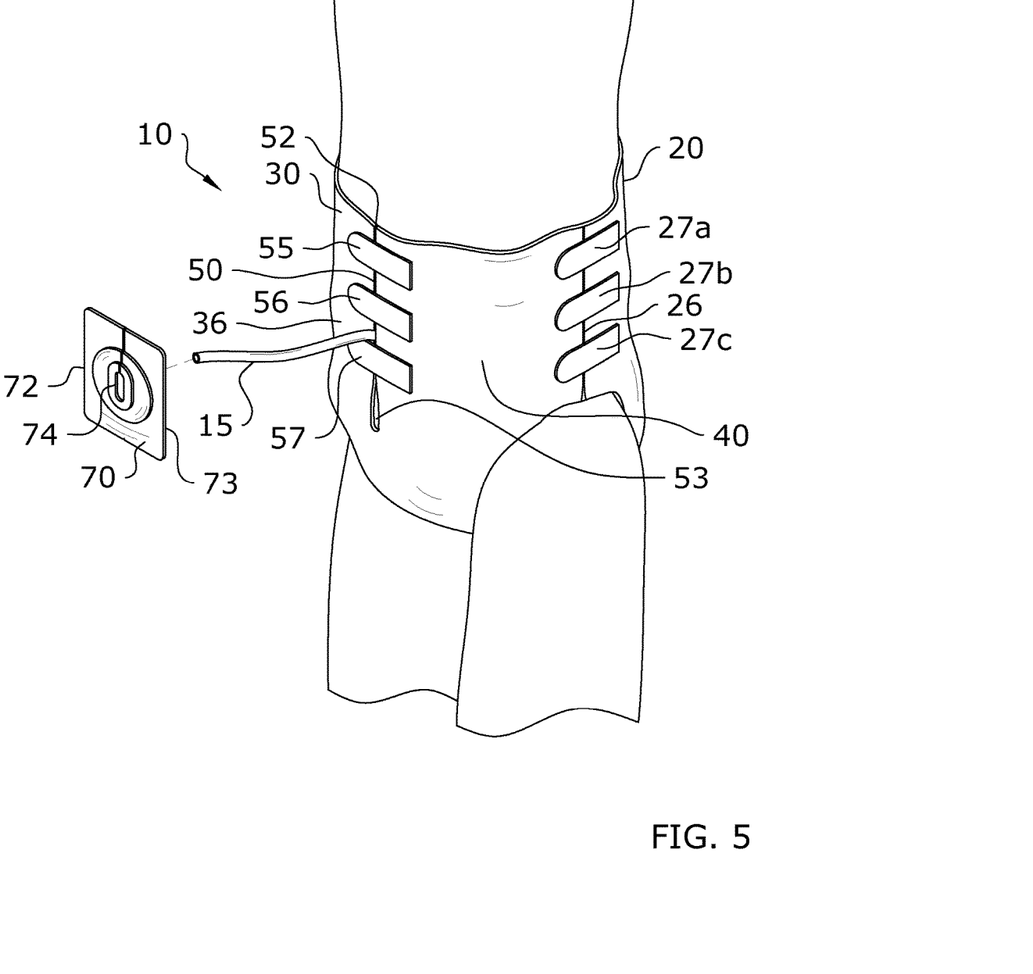
FIG. 5 is an upper perspective view of the present invention with the tube adapter aligned for placement.
Figure 6:
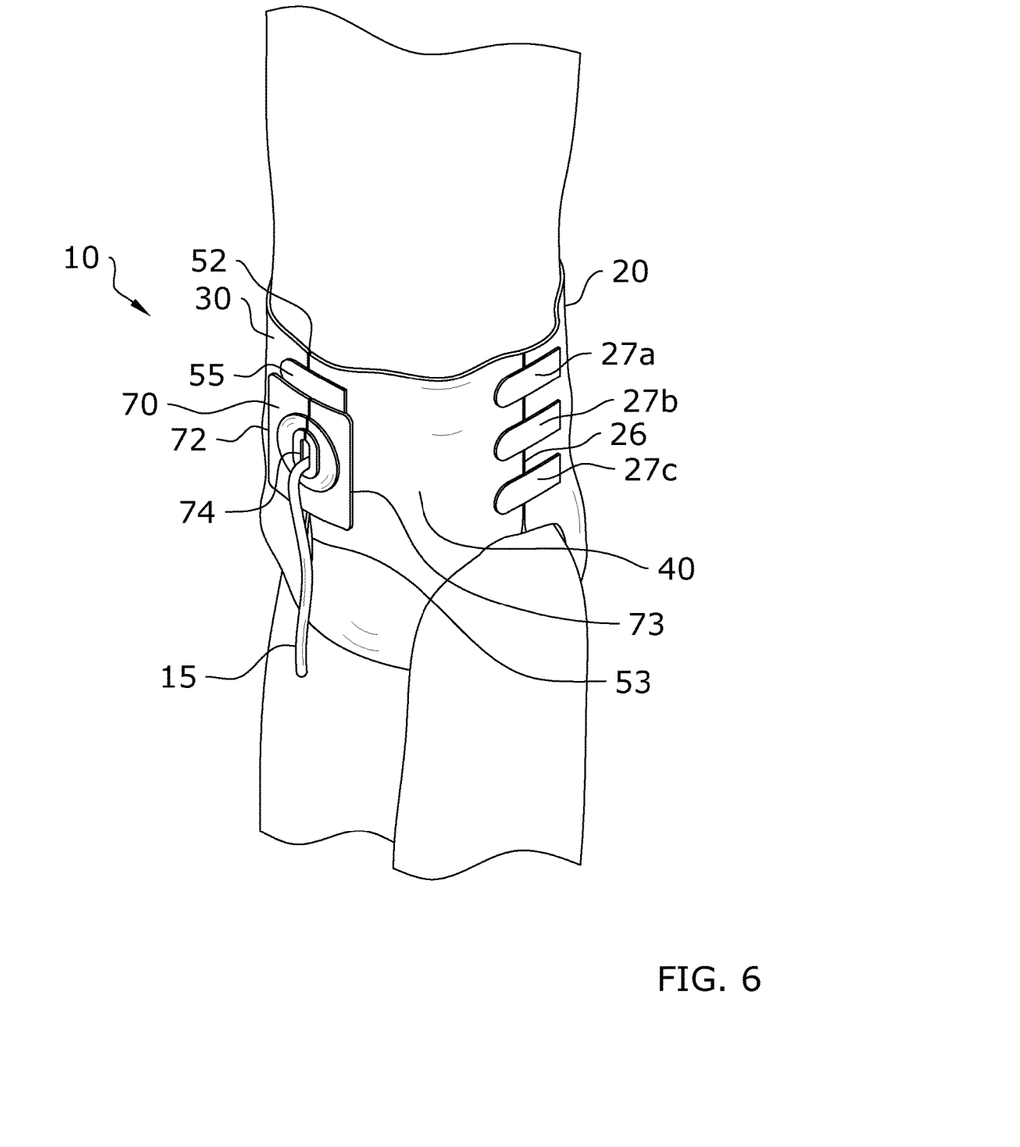
FIG. 6 is an upper perspective view of the present invention with the tube adapter installed.
Figure 7:
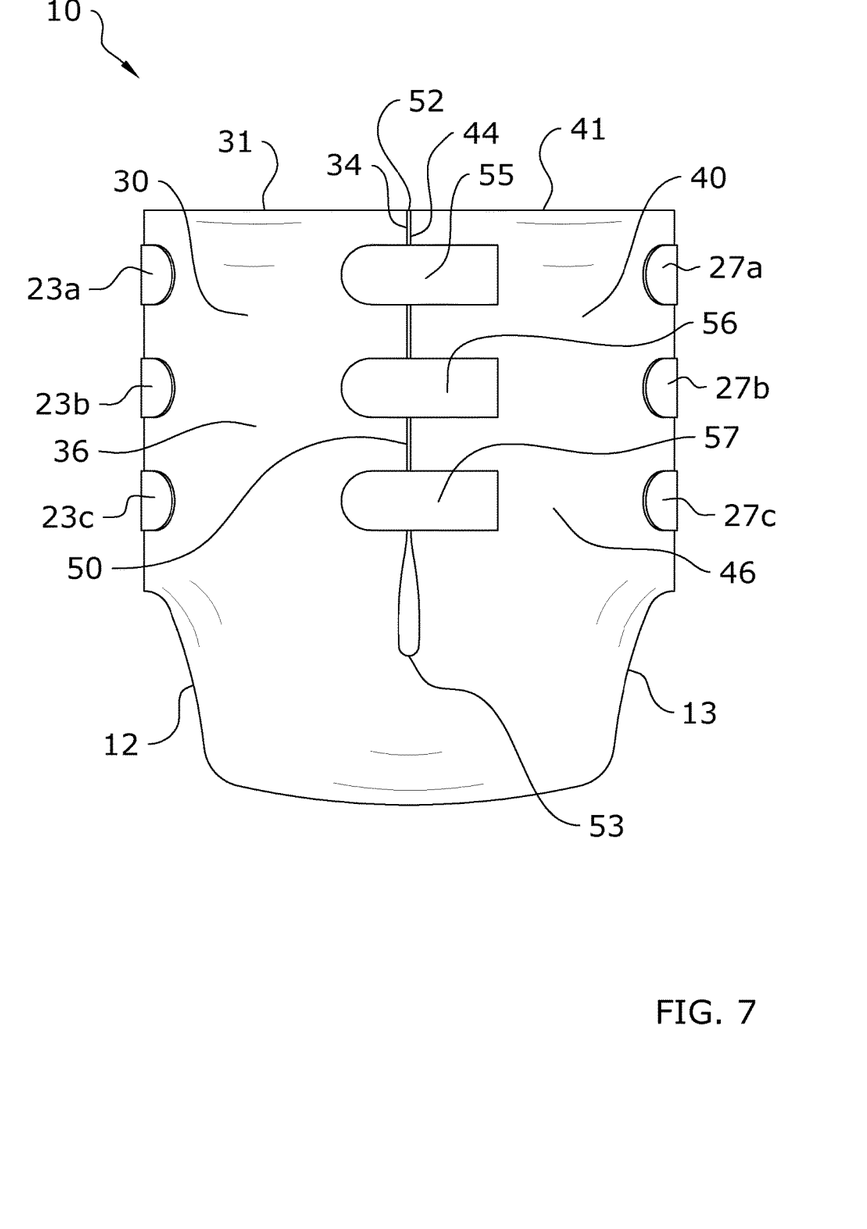
FIG. 7 is a frontal view of the present invention.

An alternate embodiment is shown in FIG. 5 which utilizes a tube adapter 70 positioned over the catheter slot 50 through which the catheter tube 15 may extend. The adapter 70 comprises a flat, semi-rectangular or round structure which includes a first side 72 secured to the first panel 30 and a second side 73 secured to the second panel 40. The respective sides may include an adhesive or hook-and-loop fastener configuration to allow the tube adapter 70 to be removably secured across the catheter slot 50. The tube adapter 70 includes a central opening 74 through which the catheter tube 15 may be positioned.

C. Operation of Preferred Embodiment.

In use, the rear portion 20 is first placed underneath the buttocks of the patient. The first panel 30 may then be extended over the groin and a first leg to be connected to the rear portion 20 via the first connectors 23a, 23b, 23c. The second panel 40 may similarly be extended over the groin and a second leg to be connected to the rear portion 20 via the second connectors 27a, 27b, 27c.

After connecting the panels 30, 40 to the rear portion 20, the catheter slot 50 may be formed by connecting the first panel 30 to the second panel 40. The slot connectors 55, 56, 57 are utilized to connect the two panels 30, 40 together to define the catheter slot 50 therebetween. The catheter tube 15 may then be extended through the catheter slot 50, either between two of the slot connectors 55, 56, 57 or above/below the set of slot connectors 55, 56, 57. A tube retainer 60 or tube adapter 70 may also be provided to guide the catheter tube 15 as it exits the undergarment 10 through the catheter slot 50.

Unless otherwise defined, all technical and scientific terms used herein have the same meaning as commonly understood by one of ordinary skill in the art to which this invention belongs. Although methods and materials similar to or equivalent to those described herein can be used in the practice or testing of the present invention, suitable methods and materials are described above. All publications, patent applications, patents, and other references mentioned herein are incorporated by reference in their entirety to the extent allowed by applicable law and regulations. The present invention may be embodied in other specific forms without departing from the spirit or essential attributes thereof, and it is therefore desired that the present embodiment be considered in all respects as illustrative and not restrictive. Any headings utilized within the description are for convenience only and have no legal or limiting effect.

The invention claimed is:

1. An undergarment with catheter support, comprising:
   a rear portion comprising an upper edge adapted to partially encircle a waist, wherein said rear portion comprises a first panel connected to a first side of said rear portion and a second panel connected to a second side of said rear portion;
   wherein said first panel comprises an upper edge, a first outer side, a first inner side, and a first lower end, wherein said first inner side of said first panel comprises a first free edge extending from said first panel upper edge to said first lower end of said first panel;
   wherein said second panel comprises an upper edge, a second outer side, a second inner side, and a second lower end, wherein said second inner side of said second panel comprises a second free edge extending from said second panel upper edge to said second lower end of said second panel, wherein said first free edge and said second free edge are removably connected to each other;
   wherein the first panel upper edge and the second panel upper edge are adapted to releasably connect to the rear portion upper edge to form an undergarment upper edge adapted to encircle the waist; and
   a catheter slot defined between said first free edge of said first panel and said second free edge of said second panel when said first free edge and said second free edge are connected, said catheter slot being adapted to provide passage for a catheter tube, wherein said catheter slot divides said first panel and second panel upper edges between said first free edge of said first panel and said second free edge of said second panel.

2. The undergarment with catheter support of claim 1, further comprising one or more slot connectors for removably connecting said first panel to said second panel.

3. The undergarment with catheter support of claim 2, wherein said one or more slot connectors is comprised of three vertically stacked slot connectors.

4. The undergarment with catheter support of claim 1, wherein said rear portion is comprised of an absorbent material.

5. The undergarment with catheter support of claim 1, further comprising a tube retainer extending between said first panel and said second panel.

6. The undergarment with catheter support of claim 5, wherein a first end of said tube retainer is connected to said first panel and a second end of said tube retainer is connected to said second panel.

7. The undergarment with catheter support of claim 6, wherein said tube retainer includes a looped portion, wherein said catheter tube extends through said looped portion.

8. A catheter support system, comprising: an undergarment including one or more absorbent portions on an internal surface of said undergarment, wherein said undergarment comprises:
   a rear portion comprising an upper edge adapted to partially encircle a waist wherein said rear portion comprises a first panel connected to a first side of said rear portion and a second panel connected to a second side of said rear portion;
   wherein said first panel comprises an upper edge, a first outer side, a first inner side, and a first lower end, wherein said first inner side of said first panel comprises a first free edge extending from said first panel upper edge to said first lower end of said first panel; and
   wherein said second panel comprises an upper edge, a second outer side, a second inner side, and a second lower end, wherein said second inner side of said second panel comprises a second free edge extending from said second panel upper edge to said second lower end of said second panel, wherein said first free edge and said second free edge are removably connected to each other;
   wherein the first panel upper edge and the second panel upper edge are adapted to releasably connect to the rear portion upper edge to form an undergarment upper edge adapted to encircle the waist;
   a catheter slot defined between said first free edge and said second free edge when said first free edge and said second free edge are connected, said catheter slot being adapted to provide passage for a catheter tube, wherein said catheter slot divides said first panel and second panel upper edges between said first free edge of said first panel and said second free edge of said second panel;

a tube retainer extending across said catheter slot, wherein said tube retainer includes a looped portion; and an indwelling catheter extending through said catheter slot, wherein a distal end of said indwelling catheter extends through said looped portion of said tube retainer.

9. The catheter support system of claim 8, further comprising one or more slot connectors for removably connecting said first panel to said second panel.

10. The catheter support system of claim 9, wherein said one or more slot connectors is comprised of two vertically stacked slot connectors.

11. The catheter support system of claim 8, further comprising a pad positioned against said internal surface of said undergarment adjacent to said catheter slot.

12. A catheter support system, comprising:

an undergarment including one or more absorbent portions on an internal surface of said undergarment, wherein said undergarment comprises:

a rear portion comprising an upper edge adapted to partially encircle a waist wherein said rear portion comprises a first panel connected to a first side of said rear portion and a second panel connected to a second side of said rear portion;

wherein said first panel comprises an upper edge, a first outer side, a first inner side, and a first lower end, wherein said first inner side of said first panel comprises a first free edge extending from said first panel upper edge to said first lower end of said first panel;

wherein said second panel comprises an upper edge, a second outer side, a second inner side, and a second lower end, wherein said second inner side of said second panel comprises a second free edge extending from said second panel upper edge to said second lower end of said second panel, wherein said first free edge and said second free edge are removably connected to each other;

wherein the first panel upper edge and the second panel upper edge are adapted to releasably connect to the rear portion upper edge to form an undergarment upper edge adapted to encircle the waist;

a catheter slot defined between said first free edge and said second free edge when said first free edge and said second free edge are connected, said catheter slot being adapted to provide passage for a catheter tube, wherein said catheter slot divides said first panel and second panel upper edges between said first free edge of said first panel and said second free edge of said second panel;

one or more slot connectors for removably connecting said first panel to said second panel;

a tube retainer extending across said catheter slot, wherein said tube retainer includes a looped portion;

a pad positioned against said internal surface of said undergarment adjacent to said catheter slot; and an indwelling catheter extending through said catheter slot, wherein a distal end of said indwelling catheter extends through said looped portion of said tube retainer.

13. The catheter support system of claim 12, wherein a first end of said tube retainer is removably connected to said first panel and wherein a second end of said tube retainer is removably connected to said second panel.

* * * * *